(12) United States Patent
Levandowski et al.

(10) Patent No.: US 11,759,536 B2
(45) Date of Patent: Sep. 19, 2023

(54) MOBILE DEVICE CASE WITH DISINFECTING MODULE

(71) Applicants: Peter Garth Levandowski, Mesick, MI (US); John Phillip Levandowski, II, Grand Rapids, MI (US)

(72) Inventors: Peter Garth Levandowski, Mesick, MI (US); John Phillip Levandowski, II, Grand Rapids, MI (US)

( * ) Notice: Subject to any disclaimer, the term of this patent is extended or adjusted under 35 U.S.C. 154(b) by 367 days.

(21) Appl. No.: 17/208,584

(22) Filed: Mar. 22, 2021

(65) Prior Publication Data

US 2021/0290794 A1   Sep. 23, 2021

Related U.S. Application Data

(60) Provisional application No. 63/100,606, filed on Mar. 21, 2020.

(51) Int. Cl.
| | |
|---|---|
| *A61L 2/10* | (2006.01) |
| *F21V 23/02* | (2006.01) |
| *A61L 2/26* | (2006.01) |
| *F21V 3/00* | (2015.01) |
| *H04B 1/3888* | (2015.01) |

(52) U.S. Cl.
CPC .................. *A61L 2/10* (2013.01); *A61L 2/26* (2013.01); *F21V 23/02* (2013.01); *H04B 1/3888* (2013.01); *A61L 2202/11* (2013.01); *A61L 2202/16* (2013.01); *F21V 3/00* (2013.01)

(58) Field of Classification Search
CPC .......... A61L 2/10; A61L 2/26; A61L 2202/11; A61L 2202/16; F21V 23/02; F21V 3/00; H04B 1/3888
USPC ........................... 250/453.11, 454.11, 455.11
See application file for complete search history.

(56) References Cited

U.S. PATENT DOCUMENTS

| | | | |
|---|---|---|---|
| 2014/0183377 A1* | 7/2014 | Bettles | A61L 2/10 |
| | | | 250/455.11 |
| 2021/0196848 A1* | 7/2021 | Baarman | A61L 2/26 |
| 2022/0023456 A1* | 1/2022 | Wojczak | A61L 2/10 |
| 2022/0023462 A1* | 1/2022 | McGill | A61L 2/26 |
| 2022/0273833 A1* | 9/2022 | Crosby | A61L 2/10 |

\* cited by examiner

*Primary Examiner* — Nicole M Ippolito
(74) *Attorney, Agent, or Firm* — MITCHELL LAW PLLC; Matthew W. Mitchell

(57) ABSTRACT

A case for a mobile device is disclosed. The case includes a housing having a portion configured to receive a mobile device, and a tethered disinfecting module selectively removeable from the housing, the tethered disinfecting module having one or more UV light emitting devices configured to selectively emit disinfecting light upon surfaces of the case and the mobile device. Various embodiments include visible and blue light for disinfecting surfaces of a mobile device and the case.

24 Claims, 9 Drawing Sheets

MOBILE DEVICE CASE WITH DISINFECTING MODULE

CROSS REFERENCE TO RELATED APPLICATIONS

This application claims the benefit of Provisional Application No. 63/100,606 filed on Mar. 21, 2020 which is hereby incorporated herein by reference.

FIELD

The subject matter of the present application is in the field of cases and covers for mobile phones and similar portable smart devices having touchscreens, keypads, and other finger-operated controls.

BACKGROUND

The statements in this section merely provide background information related to the present disclosure and may not constitute prior art.

Protective and/or decorative cases, housings, covers, "skins" and the like (hereafter "cases") for portable electronic devices such as mobile phones and tablets are well known and popular. Such cases may partly or fully cover the front face, the back face, and/or side edges of these relatively flat, thin, portable smart devices (hereafter referred to as "phones" or "mobile phones" for convenience). The cases may snap onto or over the faces of the phone, or if softer may wrap partly or fully around the phone, usually leaving certain features such as power ports, camera lenses, lights and the like exposed or accessible while the case is in place on or closed around the phone. The cases are easily opened or removed to fully use the various features of the phone, for example to expose the touchscreen.

It has been suggested to supply a phone case with a UV light feature in order to apply a disinfecting wavelength of UV light to surfaces that the phone user might have to touch throughout the day. Such surfaces could include any that a person might have reason to touch, and that the person might be concerned about touching for fear of contamination such as viruses or bacteria that can be deactivated or killed in known manner with UV light. Examples could include counters, checkout screens at retail stores, steering wheels, door handles, packages or letters, shopping cart handles, faucets, etc.

U.S. Pat. No. 9,468,695 to Liao et al shows a UV device said to include a housing having a portion configured to be removably attached to a smart device, a UV light source disposed within the housing, wherein the UV light source is configured to receive operating power from a control mechanism in response to instructions received from the smart device. In one embodiment a protective housing includes a UV light source near the camera opening, and a region for a power source, e.g. a battery. It is said that the UV light source may receive power from a smart device that is nestled within the protective housing, supposedly with a plug that plugs into a port of the smart device and draws power therefrom, or from an external battery in the housing. The smart device is said to control light from the UV light source in either case, with the housing communicating with the smart device via a wireless communication mechanism or a wired connected, e.g. a tether. That tether, however, is merely used for a communication mechanism, and not a light module.

In another embodiment in Liao et al '965, a dongle or peripheral device is said to be provided for the smart device, with a physical and/or mechanical interface for attachment onto and detachment from the smart device. The dongle includes one or more one or more UV light sources, and it is said that it may be self-powered or may be powered by the smart device, may be physically attached to the smart device in operation, and may be operated with and/or be controlled by the smart device.

The details of implementation and use of the UV light sources in the housing and the dongle embodiments of the Liao et al. '965 patent are minimal and vague, and do not appear to the present inventors to be practical, efficient, convenient or desirable for real-world use with a mobile phone and mobile phone case where it is desired to disinfect various daily surfaces, including disinfecting the surface of the phone itself and any case employed with the phone. Hence there is a need for a mobile device case with a disinfecting module as described herein.

BRIEF SUMMARY

The present disclosure includes is a UV light module incorporated into a mobile phone case in a manner which makes it useful for treating surfaces with UV light, including the surfaces of a phone used with the case and with the case itself.

The UV light module is configured with one or more UV light emitters (e.g., UV LED's of known type), the module being configured and movable both with the case and relative to the case in a way that allows it to be positioned and maneuvered to treat various surfaces apart from the phone and the case, and also to be positioned and maneuvered to treat the surfaces of the phone, the case, and any cover on the case.

In some embodiments, the UV light module is incorporated into the case in a manner so that it may be used while connected to the case, either while the case is attached to the phone or when the case is removed from the phone. In some embodiments the UV light module is concealed or covered while in the case by a case cover, and in further embodiments the case cover includes UV light-transmissive portions aligned with light-emitter elements on the UV light module in the case to allow the UV light module to treat surfaces external to the case without moving the UV light module relative to the case or removing the case cover. The UV light transmissive portions in the case cover in some embodiments may be solid "window" materials transmissive/transparent to the UV light, or may be openings of various shapes.

In some embodiments the UV light module is detachable from the case, preferably while remaining tethered to the case by a flexible cable, so that the UV light may be applied to the case itself, to any case cover opened or removed to detach the UV light module from the case, and/or to portions of the phone while the case is attached to the phone.

The case cover may be a removable piece, similar to the removable pieces for the battery area on remote controls. This may either be a clip within the parameters of the case, or a removable end, cap or part that may slide off the case in any direction. In some embodiments the UV light module is concealed within the case, underneath and independent of the removable cover. In some embodiments the case cover does not have holes, slits, transparent material, or other UV light-transmitting portions so that UV light cannot pass through.

In some embodiments the UV light module is attached to a removable case cover and is dependent on the case cover for motion. For this embodiment the LED lights can face internally or externally with respect to the case. If facing internally, UV light-transmissive features such as holes, slits or transparent material may not be needed on the case cover to align with the UV light emitter portion(s) of the UV light module.

In one embodiment, the UV light module is a substantially flat "panel", not limited in two-dimensional shape, configured to nest within a corresponding cavity or recess in the phone case, with or without a case cover. In a further embodiment, the UV light module is tethered to the case, whether the UV light module can move independently of the case cover or can move with the case cover. In a further embodiment, the UV light module tether is nested in a corresponding cable cavity in the case.

Electrical power for the UV light module may be from the mobile phone battery when the case is coupled to the phone via any known type of electrical power supplying connection, or may be from a battery incorporated into the case, or may be from a combination of a phone battery and a case battery.

"UV" is used herein to mean any wavelength, pattern, or intensity of light, visible or invisible, whether UV light or other-than-UV-light (or combinations thereof), capable of treating surfaces by reducing, de-activating, killing, making inert, or otherwise rendering viruses, bacteria, and other infectious or noxious organisms harmless (or at least less harmful or infectious) to people. For example, UVC wavelengths are germicidal, and are known to kill or inactivate micro-organisms by destroying nucleic acids and disrupting their DNA, leaving them unable to perform vital cellular functions.

In order for the UV light module to be positioned for UV light treatment of the case and phone, the UV light module needs to be pulled out and away from the case. There needs to be ample length of electrical cord (cable or wiring) for this to be possible. The cable may be very soft and flexible (non-shape-holding) in some embodiments, or the cable may be flexible but shape-holding to hold a position that it is bent to, making it possible to not have to hold the UV light module when treating the case, the phone, or other surfaces with the UV light from the module.

In some embodiments the cable may be attached to a sliding mechanism that has a knob that is accessible through a slit in the case. The knob may be attached to the cable stored in the recess of the case body. A slit or opening in the case surface allows the user to move the knob up and down, thus giving the UV light module more slack to extend the cable from the case. Also, the knob system helps retract the cable back into place when closing. The knob may have wings, parts or a cap that are/is wider than the cable slit. These wings or parts may be on the inside and or outside of the slit(s) to make sure the knob stays exposed and does not fall back into the cavity or not fit well. These wings or parts also can help the user easily slide the knob. The knob also may slide along a track system.

In some embodiments the cord may be hidden within the case and may be wound up, similar to a hose reel. In other embodiments, the cord may be simply tucked within the case recess or cavity. In another embodiment there may be an external piece to aid in winding up the cord in the case's internal reel mechanism; this piece may be present on the external surface of the case, and may have an area on the surface of the case to turn and reel in the cord as well as aiding in reeling it out. In some embodiments a slider may be used to help guide the cord into the back of the cavity. This cord will be long enough to easily extend from the case and perform UV treatment of surfaces both beyond the case and phone, as well as all surfaces of the case and phone.

In a preferred embodiment, the UV light module is a substantially flat panel stored in a mating recess in the case. A battery and a control board including the circuitry for controlling the UV light module are also stored in a mating recess or recesses in the case in a similar substantially flat manner. The UV light module is tethered by a cable to the case, the cable in electrical and control communication with the control board and battery for powering and operating the UV light module. In a further embodiment, the UV light module cable connecting the UV light module to the battery/controller in the case is stored in a close-conforming circuitous cable recess or channel in the case, in a substantially flat, substantially co-planar manner with the UV light module.

These and other features and advantages of the invention will become apparent from the detailed description below, in light of the accompanying drawings.

BRIEF DESCRIPTION OF THE DRAWINGS

One or more embodiments will now be described, by way of example, with reference to the accompanying drawings, in which.

DETAILED DESCRIPTION

Figure 1:
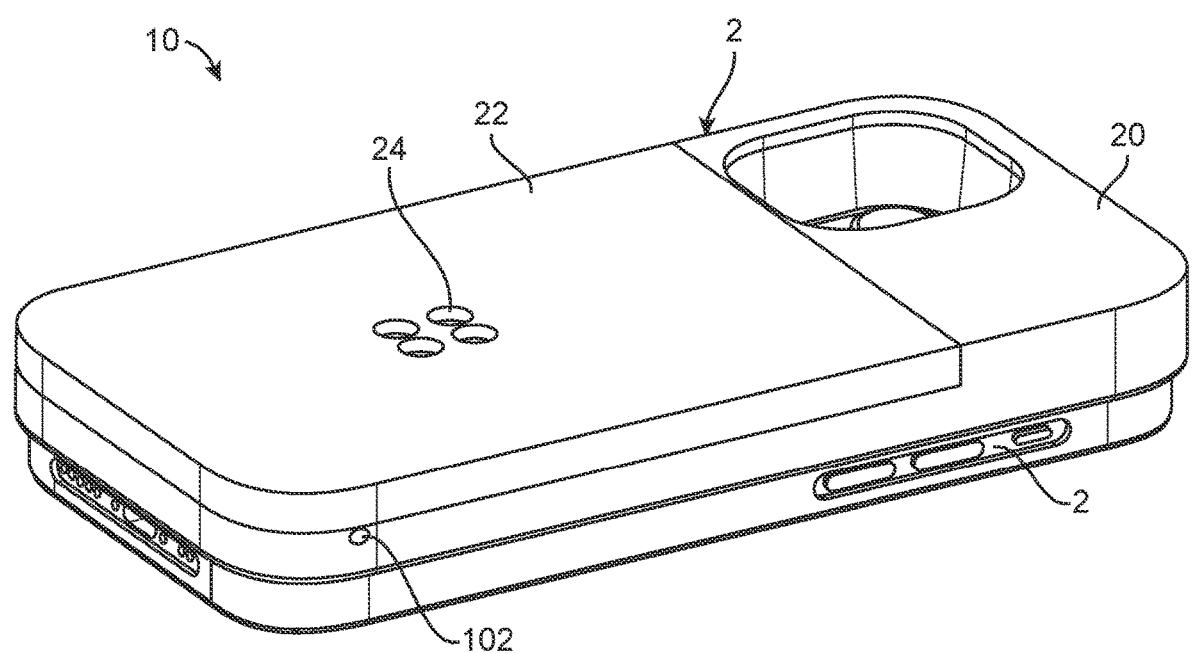
FIG. 1 shows an exemplary case partially encasing an exemplary mobile device, in accordance with the present disclosure.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment.

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

As used in the description herein and throughout the claims, the following terms take the meanings explicitly associated herein, unless the context clearly dictates otherwise: the meaning of "a," "an," and "the" includes plural reference, the meaning of "in" includes "in" and "on." The term "based upon" is not exclusive and allows for being based on additional factors not described, unless the context clearly dictates otherwise. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner.

Referring now to the drawings, wherein the depictions are for the purpose of illustrating certain exemplary embodiments only and not for the purpose of limiting the same, FIG. 1 shows an exemplary case 10 partially encasing an exemplary mobile device 2. The case 10 is preferably configured to protect the mobile device 2. The case 10 can include various apertures, openings, or recesses for accessing buttons or ports of an encased mobile device, such as shown in the exemplary case 10 for an exemplary mobile device 2. These openings, recesses, or apertures are positioned and correspond to the various components of a mobile device, such as a camera lens, power ports, user controls, buttons, etc. and allow proper operation of the mobile device 2 when inside a portion of the case 10. The case 10 includes a disinfecting module 100 shown and described hereinbelow.

The case 10 includes a housing 20 configured to contain the disinfecting module 100 and encase the mobile device 2. In one embodiment, components of the case 10, including the disinfecting module 100, may be accessed via a removeable cover 22. The removeable cover 22 may be selectively coupled to the housing 20 via an integral clip or a mechanism as known by someone skilled in the art.

In one embodiment, either the housing 20 or the removeable cover 22 includes one or more apertures 24. These apertures 24 are preferably aligned with LED lights of the disinfecting module 100, so that emitted light may pass through. In one embodiment, one or more windows of transparent or translucent material may be included to permit emitted light to pass through, but protect an inside of the case 10 from dust or other undesirable particles.

The housing 20 and the cover 22 may be integrally formed or formed of one or more components. The housing 20 and the cover 22 may be formed of one or more materials such as plastics, rubberized plastic, silicone, water resistant material, resilient material, rubber, leather, etc. In one embodiment, antimicrobial materials are used. The various components of the mobile phone case can be separate and be may be affixed with glue, acrylic glue, fasteners, snaps etc. or the components may be integral with one another. At least a portion of the housing 20 is preferably formed of a resilient material in order to secure the mobile device 2. The resilient material is configured such that a mobile device may be inserted into the case 10 and retained by securing features once bended and flexed around a mobile device. In one embodiment, a mobile device, such as the mobile device 2, can be received by and held in place in the case 10 via a friction fit. In one embodiment, when a mobile device is being positioned into the case 10 such that the back of a mobile device abuts an inner surface, outward forces act on the resilient material of the inboard facing catching feature, which may be a lip, ridge or flange that partially envelops a mobile device. A portion of the case 10 is sized such that the surfaces of a mobile device fits snug with the inside surfaces.

Figure 2:
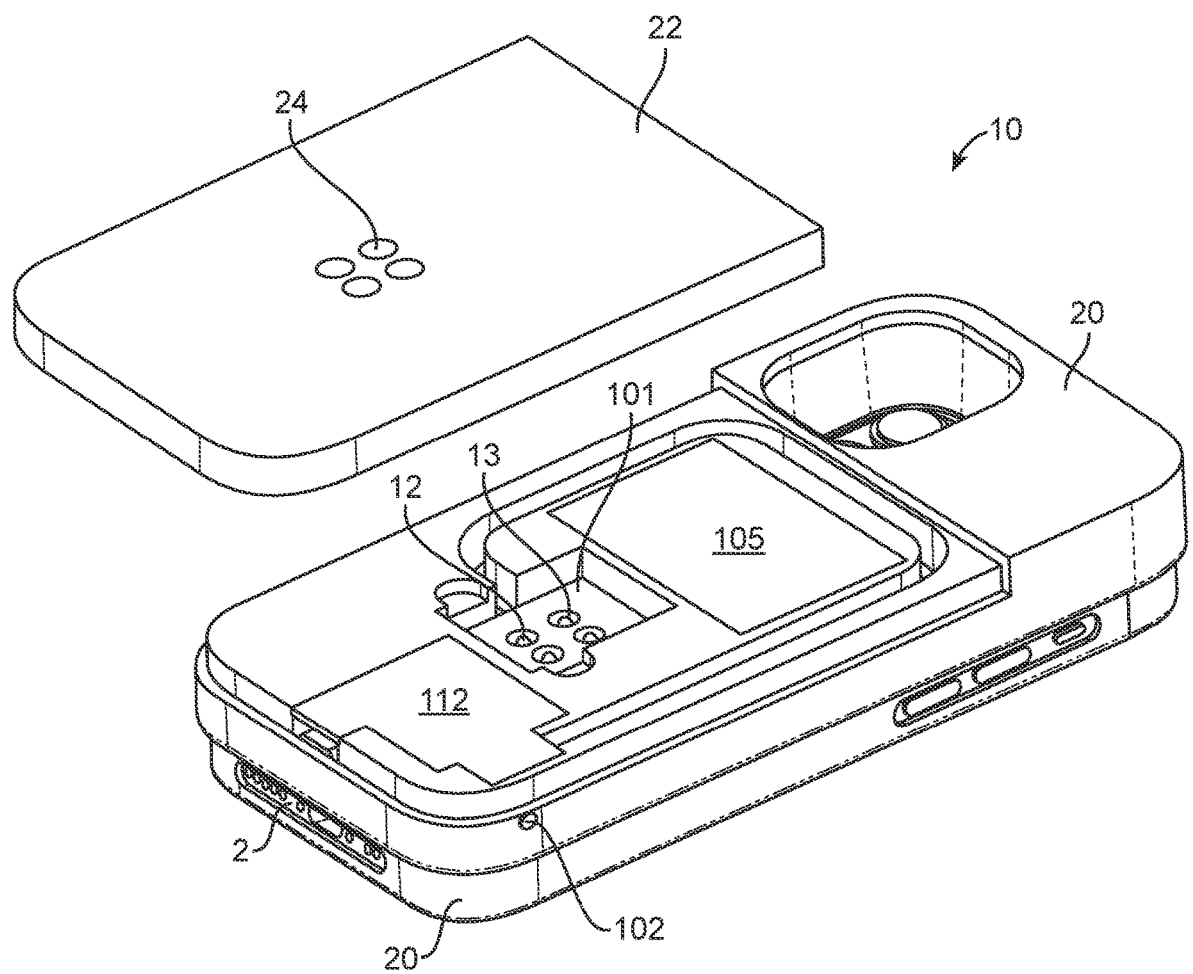
FIG. 2 shows, the case is shown with the cover removed from the housing and a mobile device secured, in accordance with the present disclosure.

With reference to FIG. 2, the case 10 is shown with the cover 22 removed from the housing 20 and a mobile device 2 secured. As FIG. 2 shows, the case 10 is configured to contain the disinfecting module 100 including the cover 101. An exemplary battery cover 105 and an exemplary processor module cover 112 may be used in various embodiments. The disinfecting module 100 includes one or more light emitting devices 12 such as an LED component. Apertures 13 can be used to permit light from the lighting devices 12 to pass through. In one embodiment, the apertures 13 can be covered with a window formed of transparent or translucent material. In one embodiment, the apertures 13 axially align with the apertures 24 of the cover 22. As FIG. 2 shows, the case 10 includes a recess sized and shaped to selectively receive the disinfecting module 100.

Figure 3:
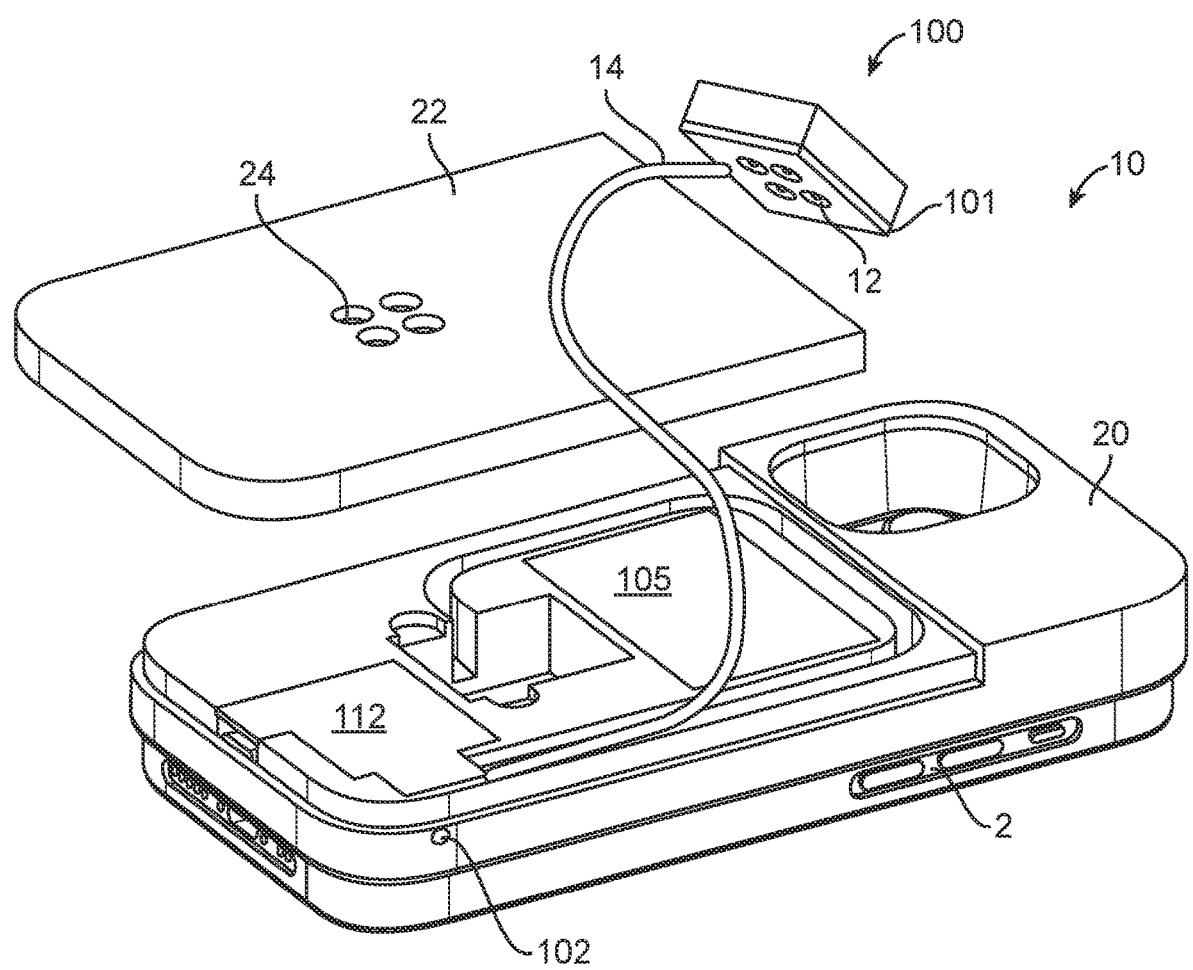
FIG. 3, the case is again shown with the cover removed from the housing and a mobile device secured, but also the disinfecting module removed from the recess of the case, in accordance with the present disclosure.

With reference to FIG. 3, the case 10 is again shown with the cover 22 removed from the housing 20 and a mobile device 2 secured, but also the disinfecting module 100 removed from the recess of the case 10. As FIG. 3 shows, the disinfecting module 100 receives power and instructions via a tethered electric cord 14. In one embodiment, the cord 14 may be stored in another recess of the case 10. In some embodiments the cord 14 may be wound up. In another embodiment there is an external piece to aid in winding up the cord in the case's internal reel mechanism. This piece may be present on the external surface of the case. This piece may have an area on the surface of the case to turn and reel in the cord as well as aiding in reeling it out. In some embodiments a slider is used to help guide the cord into the back of the cavity. The cord 14 should be long enough to extend from the case 10 and perform sanitation on the mobile device 2. The cord 14 may be able to bend and keep the position it is bent to allow the user to easily direct the light(s) at the desired surface to sanitate. In some embodiments, the cord 14 includes a bendable sheath with electrical(s) wires within.

As FIGS. 2 and 3 show, the disinfecting module 100 includes one or more light emitting devices 12. The exemplary figures show the disinfecting module 100 with four light emitting devices 12, but it is contemplated herein that any number of light emitting devices 12 may be used in various embodiments. The light emitting devices 12 are orientated on the disinfecting module 100 such that the light from the light emitting devices 12 may be directed outward. Examples of light emitting devices 12 may include light emitting diodes (LED), organic LEDs (OLEDs), UV-C LEDs, UV-A LEDs, semiconductor dies, LEDs with light converting material(s)/layer(s), electroluminescent wires, electroluminescent sheets, flexible LEDs, light emitting layers, etc. A light emitting device 12 may comprise of a single LED. The light emitting devices 12 may be configured to emit light blue light (e.g., wavelength range of 420 nm-510 nm) and/or ultraviolet light (e.g., wavelength range of 10 nm-400 nm). In some embodiments, visible spectrum light is also included as an LED so that a user can: (1) readily see that the disinfecting module 100 is at an ON operating state; and (2) know about where the disinfecting light is being directed. In some embodiments, visible spectrum light, such as green, violet or purple is used. In some embodiments, the black light, from, e.g., an UV-A LED, can be used to identify places on the case 10 or mobile device 2 that require disinfecting light energy. In some embodiments, the light emitting devices 12 may be used synergistically to both inactivate viral and undesirable microorganisms. Various example methods, devices, and systems described herein may use one or both of blue light and ultraviolet light sources.

Figure 4:
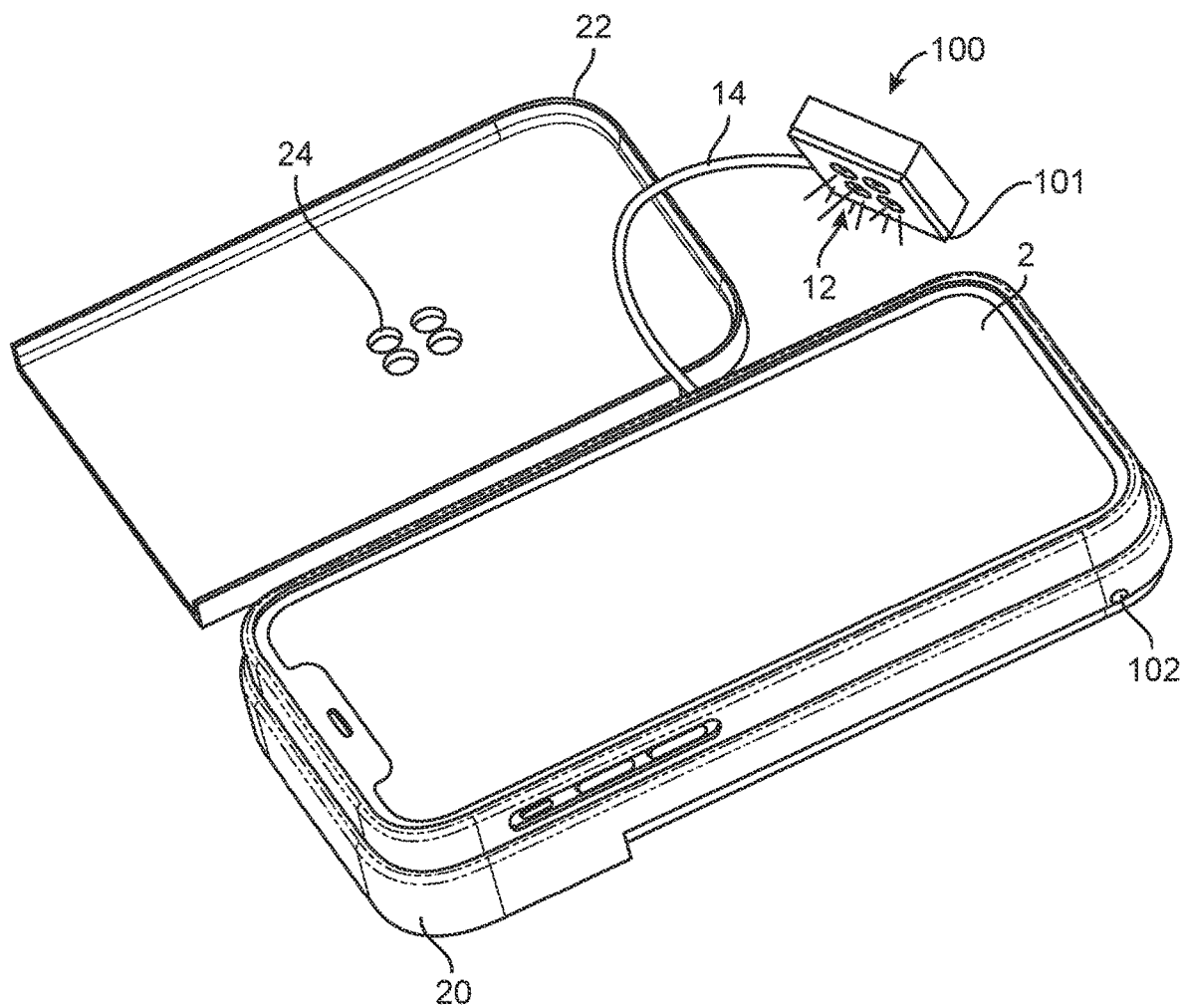
FIG. 4 shows an exemplary view of the disinfecting module in use on a surface of the mobile device, that is partially encased within the case, in accordance with the present disclosure.

FIG. 4 shows an exemplary view of the disinfecting module 100 in use on a surface of the mobile device 2, that is partially encased within the case 10. As FIG. 4 shows, a user may remove the disinfecting module 100 from the case 10, and then direct the light emitting devices 12 of the disinfecting module 100 at the surface of the mobile device 2. In this way, the light emitting devices 12 can disinfect and/or sanitize the surface of the mobile device 2 or the case 10 itself. As one skilled in the art will recognize, UVC wavelengths are germicidal and may be used to kill or inactivate microorganisms by destroying nucleic acids and disrupting their DNA. Thereby, leaving them unable to perform vital cellular functions, which may make them infectious or capable of spreading disease. In various embodiments, one or more of the light emitting devices 12 may be configured to emit blue lights which may inactivate or sanitize surfaces. In one embodiment, the light emitting devices 12 may be configured to pulse light energy. In one embodiment, the light emitting devices 12 may be controlled to alternate spectrums of light such as alternating between ultraviolets light and blue lights.

Figure 5:
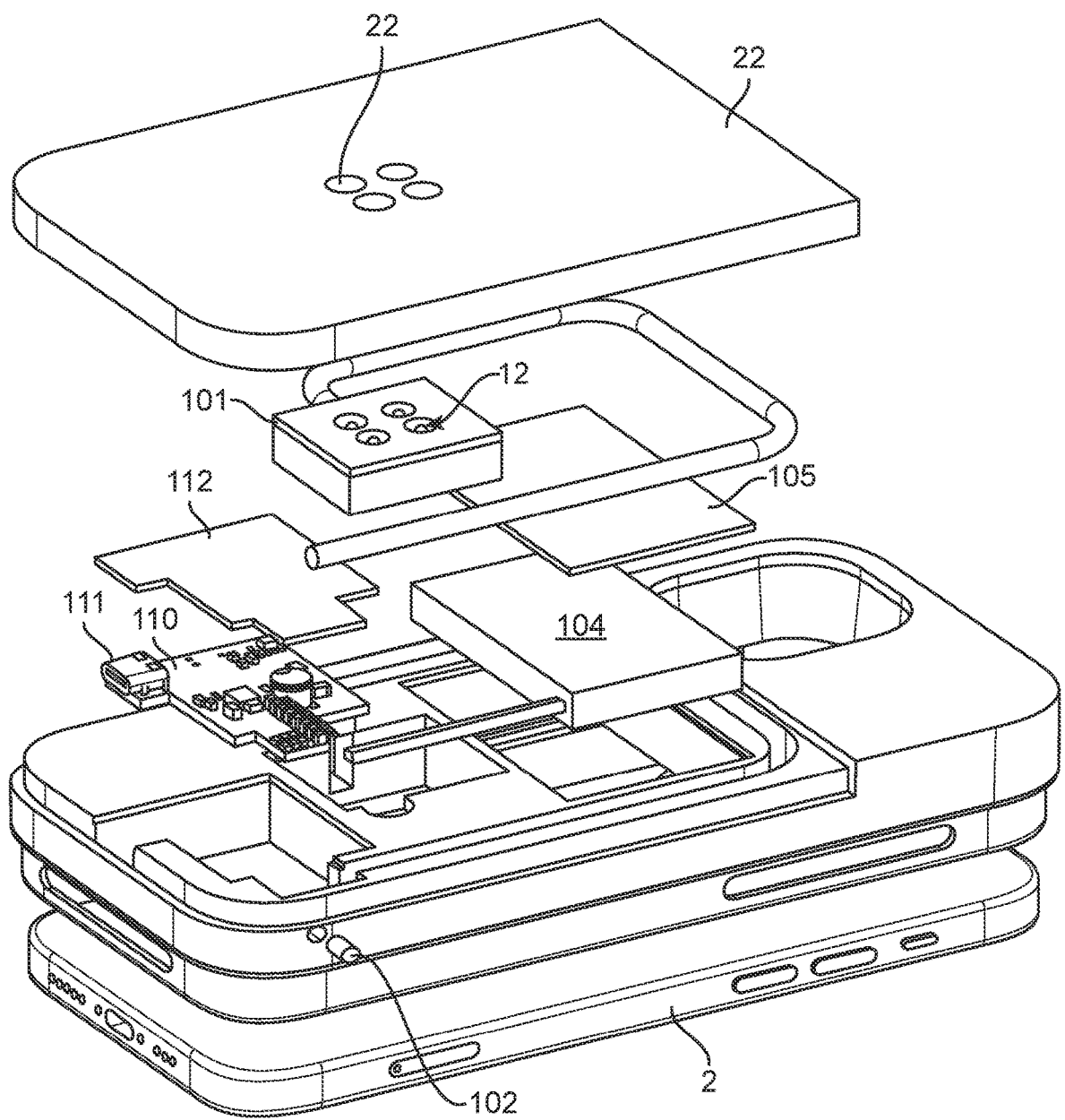
FIG. 5 shows an exemplary exploded view of the case and the exemplary mobile device, in accordance with the present disclosure.

FIG. 5 shows an exemplary exploded view of the case 10 and the exemplary mobile device 2. As FIG. 5 shows, the case 10 can include a processor module 110 and a power source 104. The processor module 110 preferably includes a port 111, which may be used to recharge the power source 104. A push button 102 is shown in the figures as well. The push button 102, may abut another button on the processor module 110 when the processor module 110 is secured within one of the recesses of the case 10. In this way, a user may actuate the disinfecting module 100 via the push button 102.

In one embodiment, the port 111 may be selectively connected to the mobile device in order to obtain electric power. In one embodiment, the case 10 includes a port to attach to 3rd party items via their ports such as chargers. In one embodiment, the mobile device 2 can be charged when it is within the case 10 via induction elements within the case via power from the power source 104. In various embodiments, the case 10 may also use a combination of the mobile device's power and the additional battery embedded in the case 10. The case 10 may have its own separate port to power its embedded battery 104. The case 10 may also have solar panels and cells to power its batteries and or the mobile device's battery(s). The case 10 may wirelessly connect to the mobile device's battery to power the lights 12 through electromagnetic induction.

Figure 6:
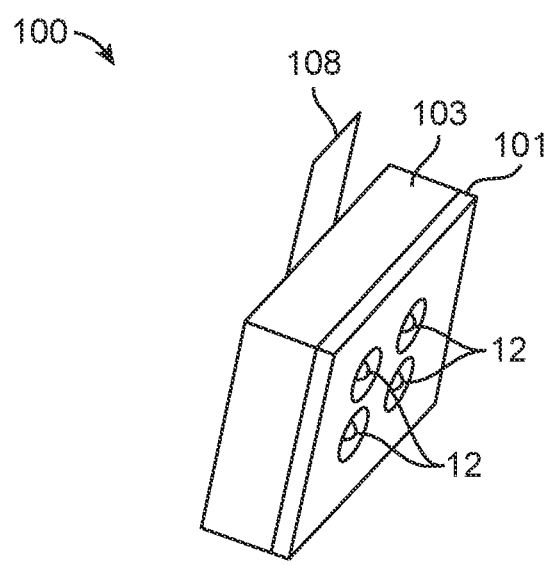
FIGS. 6 and 7 show exemplary embodiments of the tethered disinfecting module, in accordance with the present disclosure.
Figure 7:
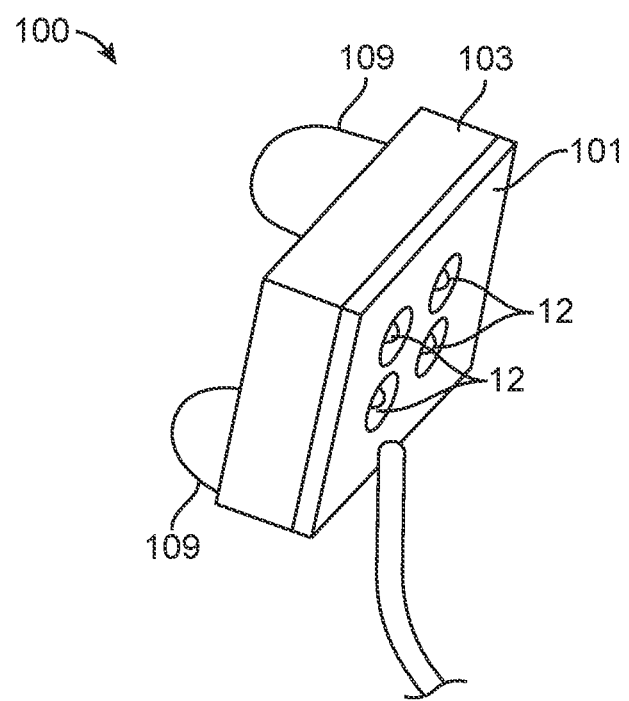

FIGS. 6 and 7 show embodiments of the disinfecting module 100 depicting an exemplary handle 108 as shown in FIG. 6 and loops 109 as shown in FIG. 7. The loops 109 and the handle 108 may be used in various embodiments to aid a user in removing the disinfecting module 100 from a recess of the case 10 or holding the disinfecting module 100 while disinfecting surfaces of the case 10 or the mobile device 2. As FIGS. 6 and 7 show, the disinfecting module 100 can include a cover 101 that may be used to protect a circuit board having the lighting devices 12. In various embodiments, a heat shield or heat dissipator may be incorporated into the disinfecting module 100. In one embodiment, the disinfecting module 100 includes a housing 103 to contain the lighting devices 12 and any electrical components. The housing 103 preferably includes desirable thermal heat dissipation properties. The housing 103 can be formed of transparent or translucent material.

Figure 8:
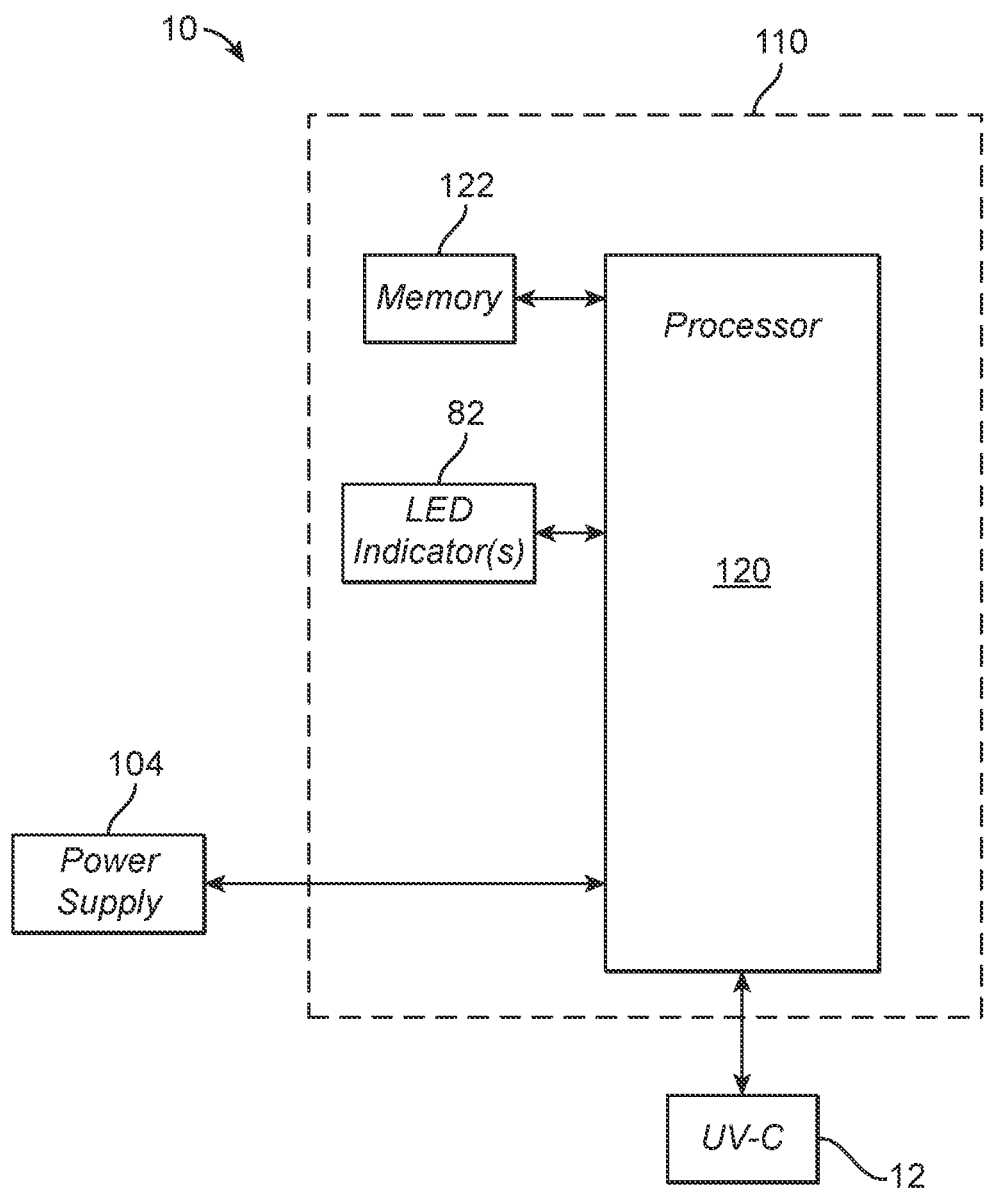
FIG. 8 schematically shows the case, in accordance with the present disclosure.

FIG. 8 schematically shows the case 10. As shown in FIG. 6, the case 10 includes a processor module 110. The processor module 110 may include any digital and/or analog circuit elements, comprising discrete and/or solid state components, suitable for use with the embodiments disclosed herein. In one embodiment, the processor module 110 includes a processor 120

The processor 120 may be configured to execute various computer programs (e.g., software, firmware, or other code) such as application programs and system programs to provide computing and processing operations for the case 10. In various embodiments, the processor 120 may be implemented as a host central processing unit ("CPU") using any suitable processor or logic device, such as a general purpose processor, or other processing device in alternative embodiments configured to provide processing or computing resources to the case 10. For example, the processor 120 may be responsible for executing various computer programs such as application programs and system programs to provide computing and processing operations for the case 10. The computer programs may be stored as firmware on a memory associated with processor 120, may be loaded by a manufacturer during a process of manufacturing the case 10, and may be updated from time to time with new versions or software updates via wired or wireless communication.

System programs assist in the running of a computer system. System programs may be directly responsible for controlling, integrating, and managing the individual hardware components of the computer system. Examples of system programs may include, for example, an operating system, a kernel, device drivers, programming tools, utility programs, software libraries, an application programming interface ("API"), a GUI, and so forth.

The processor module 120 may be coupled to one or more light-emitting diodes (LEDs) 82 configured to emit light in the visible spectrum. In one embodiment, a first LED of the one or more LEDs is used to indicate a first status such as a status indicating that the light emitting devices 12 are emitting light. In various embodiments, some electrical components protrude outside of the case 10.

A memory module 122 is preferably coupled to the processor 120. In various embodiments, the memory module 122 may be configured to store one or more computer programs to be executed by the processor 120. The memory module 122 may be implemented using any machine-readable or computer-readable media capable of storing data such as volatile memory or non-volatile memory, removable or non-removable memory, erasable or non-erasable memory, writeable or re-writeable memory, and so forth. Although the memory module 122 is shown as being separate from the processor 120 for purposes of illustration, in various embodiments some portion or the entire memory module 122 may be included on the same integrated circuit as the processor 120. Alternatively, some portion or the entire memory module 122 may be disposed on an integrated circuit or other medium (e.g., solid state drive) external to the integrated circuit of the processor 120.

A power source 104 configured to supply and manage power to components of the case 10 is preferably coupled to the processor 120. In one embodiment, the power source 104 is fixed and not removeable. In various exemplary embodiments, the power source 104 may be implemented by a rechargeable battery, such as a removable and rechargeable lithium ion battery to provide direct current ("DC") power, and/or an alternating current ("AC") adapter to draw power from a standard AC main power supply.

The light emitting device 12 may be electronically connected to the processor 120 or, in some embodiments, the processor module 110. In one embodiment, a step-up power converter, i.e., a boost converter may be used to increase power to the light emitting devices 12.

Figure 9:
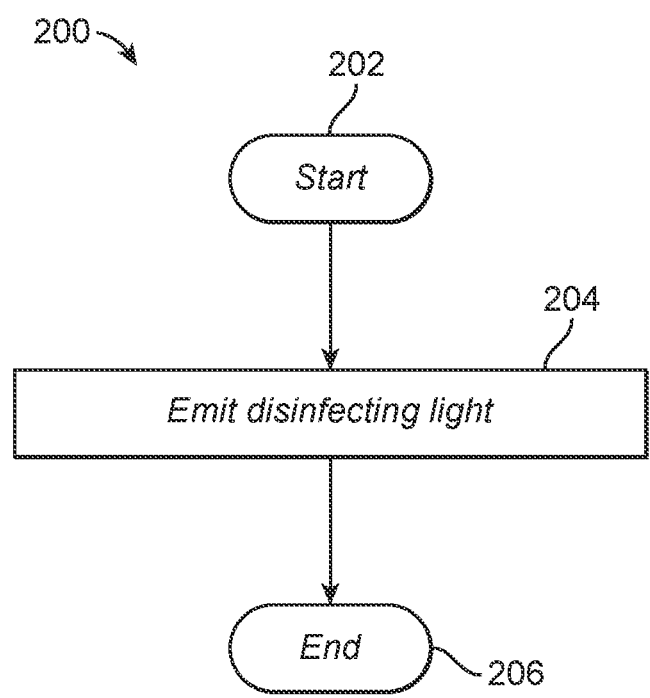
FIG. 9 shows an exemplary process for emitting disinfecting light from the light emitting devices, in accordance with the present disclosure.

FIG. 9 shows an exemplary process 200 the processor module 110 can execute for emitting disinfecting light from the light emitting devices 12. As FIG. 7 shows, the exemplary process is initiated at step 202 by a user, which can be via input from the push button 102. The processor module 110 at step 204 can then either: (1) emit light from the light emitting devices 12 until another input from the bush button 102; or (2) emit light from the light emitting devices 12 for a pre-defined duration. When emitting light, the processor module 110 can operate in one of several modes including: (1) emitting a steady, continuous emission of disinfecting light; (2) emitting pulses of disinfecting light; (3) emitting disinfecting light according to a pre-defined sequence of different types of light, e.g., ultraviolet, black light, blue light, etc., such as simultaneously emitting ultraviolet, black light, or blue light or alternating between ultraviolet, black light, or blue light disinfecting light emissions; or (4) or switching among these operating modes. After completing step 204, the processor module 110 can terminate emitting disinfecting light. In one embodiment, the user may switch between operating modes by toggling the push button 102.

In one embodiment, the push button 102 can be pushed more than once to turn the light emitting devices 12 on and or off. In one embodiment, the case 10 may have separate control buttons to toggle between operating modes or toggle different light types ON or OFF. Having a user have to push a button more than once helps with accidentally activating the light. Also having a user need to push two or more buttons helps with this as well. The on/off feature may also be controlled by an app that may be controlled on a mobile device.

Examples in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing.

It will finally be understood that the disclosed embodiments represent presently preferred examples of how to make and use the invention, but are intended to enable rather than limit the invention. Variations and modifications of the illustrated examples in the foregoing written specification and drawings may be possible without departing from the scope of the invention. It should further be understood that to the extent the term "invention" is used in the written specification, it is not to be construed as a limiting term as to number of claimed or disclosed inventions or discoveries or the scope of any such invention or discovery, but as a term which has long been used to describe new and useful improvements in science and the useful arts. The scope of the invention should accordingly be construed by what the above disclosure teaches and suggests to those skilled in the art, and by any claims that the above disclosure supports in this application or in any other application claiming priority to this application.

The invention claimed is:

1. A case for a mobile device, the case comprising:
a housing having a portion configured to receive a mobile device;
a tethered disinfecting module selectively removeable from the housing, the tethered disinfecting module having one or more UV light emitting devices configured to selectively emit disinfecting light upon surfaces of the case and the mobile device.

2. The case of claim 1, wherein the tethered disinfecting module further comprises a visible light device.

3. The case of claim 1, wherein the housing comprises one or more apertures aligned with the one or more UV light emitting devices.

4. The case of claim 1, wherein the tethered disinfecting module further comprises a blue light device.

5. The case of claim 1, wherein the tethered disinfecting module is electronically connected to a power source within the case.

6. The case of claim 1, wherein the tethered disinfecting module is electronically connected to a power source within the case, via an electrical wire encased in a sheath, the sheath being bendable into a fixed position.

7. The case of claim 1, wherein the tethered disinfecting module pulse is configured to selectively emit a continuous stream of ultraviolet light.

8. The case of claim 1, wherein the tethered disinfecting module pulse is configured to selectively emit a pulse of ultraviolet light.

9. The case of claim 1, wherein the tethered disinfecting module pulse is configured to selectively emit a continuous stream of ultraviolet light.

10. The case of claim 1, wherein the tethered disinfecting module pulse is configured to selectively emit a pre-defined sequence of ultraviolet and blue light.

11. The case of claim 10, wherein the tethered disinfecting module pulse is configured to selectively, simultaneously emit ultraviolet and blue light.

12. The case of claim 10, wherein the tethered disinfecting module pulse is configured to selectively, simultaneously emit visible light.

13. The case of claim 10, wherein the tethered disinfecting module pulse is further configured to selectively, simultaneously emit UV-A light.

14. The case of claim 11, wherein the tethered disinfecting module pulse is further configured to selectively, simultaneously emit black light.

15. A case for a mobile device, the case comprising:
a housing having a portion configured to receive a mobile device, wherein the housing comprises a first set of one or more apertures;
a tethered disinfecting module selectively removeable from the housing, the tethered disinfecting module having one or more UV light emitting devices configured to selectively emit disinfecting light upon surfaces of the case and the mobile device, wherein the tethered disinfecting module further comprises a visible light device, wherein the tethered disinfecting module includes a cover having a second set of one or more apertures axially aligned with the one or more UV light emitting devices;
a power source disposed within the housing, wherein the tethered disinfecting module is electronically connected to the power source within the case; and
wherein the first set of one or more apertures are axially aligned with the second set of one or more apertures.

16. The case of claim 15, wherein the tethered disinfecting module further comprises a blue light device.

17. The case of claim 15, wherein the tethered disinfecting module is electronically connected to a power source within the case, via an electrical wire encased in a sheath, the sheath being bendable into a fixed position.

18. The case of claim 17, wherein the tethered disinfecting module comprises handles.

19. The case of claim 17, wherein the tethered disinfecting module comprises loops.

20. The case of claim 17, wherein the tethered disinfecting module further comprises a black light device.

21. The case of claim 17, wherein the tethered disinfecting module further comprises a visible light device.

22. The case of claim 17, wherein the tethered disinfecting module further comprises a black light and a visible light device.

23. The case of claim 15, wherein the first set of one or more apertures include a transparent or translucent window.

24. The case of claim 15, wherein the second set of one or more apertures include a transparent or translucent window.

\* \* \* \* \*